United States Patent [19]

Cavitt

[11] 4,046,783

[45] Sept. 6, 1977

[54] METHOD OF OLEFIN EPOXIDATION

[75] Inventor: Stanley B. Cavitt, Austin, Tex.

[73] Assignee: Texaco Development Corporation, New York, N.Y.

[21] Appl. No.: 598,498

[22] Filed: July 23, 1975

Related U.S. Application Data

[60] Continuation-in-part of Ser. No. 382,919, July 26, 1973, abandoned, which is a division of Ser. No. 102,227, Dec. 28, 1970, Pat. No. 3,956,180.

[51] Int. Cl.$^2$ .......................................... C07D 301/06
[52] U.S. Cl. ............................................... 260/348.33
[58] Field of Search ................................ 260/348.5 V

[56] References Cited

U.S. PATENT DOCUMENTS

| | | | |
|---|---|---|---|
| 3,122,569 | 2/1964 | Kaman | 260/348.5 L |
| 3,434,975 | 3/1969 | Sheng | 252/431 |
| 3,480,563 | 11/1969 | Bonetti et al. | 252/431 |
| 3,489,775 | 1/1970 | de Roch et al. | 260/348.5 L |
| 3,597,459 | 8/1971 | Mimoun et al. | 260/429 |
| 3,668,227 | 6/1972 | Mattucci et al. | 260/429 J |
| 3,778,451 | 12/1973 | Poite | 260/348.5 L |

FOREIGN PATENT DOCUMENTS

| | | |
|---|---|---|
| 1,459,880 | 10/1966 | France |
| 1,505,337 | 11/1967 | France |

*Primary Examiner*—Norma S. Milestone
*Attorney, Agent, or Firm*—Walter D. Hunter; Carl G. Ries; Thomas H. Whaley

[57] ABSTRACT

An improved method is disclosed for the liquid phase epoxidation of an olefin to the corresponding oxirane which includes intimately contacting an olefin compound with molecular oxygen in the presence of a suitable solvent and a catalytically effective amount of a molybdenum containing catalyst material at a temperature of from about 210° C to about 270° C under a pressure sufficient to maintain the reactants, products and by-products substantially in liquid phase.

The molybdenum containing catalyst material is characterized as an oxidized alkyl molybdate complex which is substantially soluble in the reaction mixture containing the olefin, solvent, products and by-products. The molybdenum containing catalyst material is prepared by contacting an inorganic molybdenum compound with an aliphatic monohydric alcohol, in the presence of an effective amount of a weak base, to form a lower oligomeric alkyl molybdate compound. The lower oligomeric alkyl molybdate compound is then oxidized in the presence of an oxidizing amount of molecular oxygen to form the oxidized alkyl molybdate complex catalyst.

5 Claims, No Drawings

METHOD OF OLEFIN EPOXIDATION

CROSS REFERENCE TO RELATED APPLICATIONS

This application is a continuation-in-part of application Ser. No. 382,919 filed July 26, 1973, now abandoned, which is a divisional of application Ser. No. 102,227 filed Dec. 28, 1970, now U.S. Pat. No. 3,956,180.

BACKGROUND OF THE INVENTION

1. Field of the Invention

This invention relates to liquid phase molybdenum catalyzed epoxidation reactions; and, more particularly, to the liquid phase epoxidation of olefins with molecular oxygen in the presence of an oxidized alkyl molybdate complex catalyst material.

2. Prior Art

Oxiranes or epoxides, while being valuable commercial products in and of themselves, are also commercially valuable as starting reactants for synthesizing, for example nontoxic antifreeze and urethane grade polyols. Over the years, many methods have been disclosed for synthesizing such compounds. The majority of these methods involve the oxidation of the corresponding olefin. For example, it is known that ethylene can be converted to the corresponding epoxide by a vapor phase partial oxidation with molecular oxygen over silver catalyst. The ease of olefin oxidation, however, varies greatly depending upon the size and structure of the olefinic starting reactant. Further, it has been disclosed that molecular oxygen can be utilized in the liquid phase epoxidation of olefins. Additionally, various catalysts have been found to expedite these epoxidation reactions.

Recently, it has been disclosed that molybdenum and/or tungsten containing compounds are effective in the liquid phase molecular oxygen epoxidation of olefins. Specifically, soluble molybdenum and tungsten catalytic substances of naphthenates, stearates, octoates and carbonyls are disclosed as being particularly preferred molybdenum and tungsten compounds for epoxidation of olefins. See for example Koller et al (French Pat. No. 1,459,880).

Additionally, it is known that metal compounds of titanium, zirconium, hafnium, vanadium, niobium, tantalum, molybdenum and tungsten are generally effective as catalysts in the liquid phase catalytic oxidation of olefins with molecular oxygen. Metal compounds such as oxides, acids including heteropoly acids or salts, or organic esters thereof, salts of organic acids, hydroxides, hydrated oxides, inorganic salts, organic complexes, carbonyls, and anhydrides are all disclosed as being suitable. See generally Allison (U.S. Pat. No. 3,259,638). In general, however, these compounds, and particularly the organic-based materials, are the simple metal compounds having one or two metal moieties per molecule. Additionally, the majority of these compounds are substantially insoluble in the reaction medium and generally show a low rate of reactant conversion to olefin when used as a catalyst. For example, in Table 1 of Allison, it is shown that all of the metal compounds were substantially inferior in conversion to vanadium metal itself.

Giovanni A. Bonetti et al (U.S. Pat. No. 3,480,563) discloses organic-soluble molybdenum compounds derived from a direct reaction between molybdic oxide and an alcohol. Molybdenum trioxide is taught as the only preferred starting material.

The above catalyst materials suffer from various disadvantages, including poor solubility in the reaction medium, and a low metal concentration. Thus, only small amounts of a catalyst metal are carried to the reaction medium in the catalytic compound. A large excess of the catalyst is then required to give acceptable reaction times. A large amount of catalyst material has been shown detrimental to the remaining steps of the process. Additionally, these compounds evidently undergo some decomposition at higher temperatures, causing a catalyst sludge or residue to form in the reactor. This sludge formation not only decreases catalyst activity, but presents a clean out problem which contributes substantially to the down time of the production facility. Further, many of the above catalyst compounds are known to form sludge and decomposition products upon standing at room temperature. Additionally, many of these catalyst compositions are not reproducible. Thus, different results are obtained when using a like catalyst from different batches or production lots.

Unexpectedly, it has now been found that certain molybdenum containing substances are extremely effective in catalyzing liquid phase epoxidation of an olefin with molecular oxygen to yield the corresponding oxirane. Surprisingly, these substances, which may be generally characterized as oxidized alkyl molybdate complexes, expedite a high conversion of the olefin to the corresponding oxirane, are unexpectedly stable at higher reaction temperatures and produce minimal amounts of sludge or residue in the reactor. Additionally, because of the ability of these substances to withstand relatively higher reaction temperatures, excellent yields of the desired product are obtained at relatively higher temperatures than heretofore known. Further, the method of the instant invention is highly economical owing to good conversion rates utilizing very short holding times.

SUMMARY OF THE INVENTION

According to the broad aspect of the invention, an olefinically unsaturated compound is epoxidized to the corresponding oxirane in liquid phase by intimately contacting the olefinically unsaturated compound with an epoxidizing amount of a molecular oxygen epoxidizing agent in the presence of a solubilizing amount of a suitable nonpolar solvent and a catalytically effective amount of a molybdenum containing substance at epoxidizing temperatures of about 210° C to 270° C and at pressures sufficient to maintain the reaction mixture, consisting essentially of the olefin solvent and products substantially in liquid phase.

The molybdenum containing catalyst material can be generally characterized as an oxidized alkyl molybdate complex which is substantially soluble in the reaction mixture containing the olefin, solvents, and products.

The oxidized alkyl molybdate complex catalyst is prepared by intimately contacting an inorganic molybdenum compound with an aliphatic monohydric alcohol in the presence of an effective amount of a weak base to form a lower oligomeric alkyl molybdate compound. The lower oligomeric alkyl molybdate compound is then oxidized in the presence of an oxidizing amount of molecular oxygen to form the oxidized alkyl molybdate complex catalyst.

DESCRIPTION OF THE PREFERRED EMBODIMENT

In accordance with a preferred embodiment, lower olefins are epoxidized to the corresponding oxiranes by contacting and admixing the lower olefin with pure oxygen gas in the presence of a solubilizing amount of an aromatic hydrocarbon or chlorinated aromatic hydrocarbon solvent and a catalytically effective amount of the oxidized alkyl molybdate complex at temperatures of from about 230° C to 250° C and at pressures in the range of 100 atmospheres.

The catalyst material that can be utilized in the inventive method, can best be characterized as an oxidized alkyl molybdate complex which contains greater than about 20% molybdenum by weight per complex unit and is generally soluble in the epoxidation reaction mixture including reactants, solvents, products, and by-products. Preferably, the oxidized alkyl molybdate complex contains greater than about 30% molybdenum by weight per complex unit. As added to the epoxidation mixture, the dissolved catalyst material, as hereinafter more particularly described, preferably contains from about 3% to about 20% molybdenum by weight.

The catalyst material can be more particularly defined in terms of its method of preparation. The oxidized alkyl molybdate complex catalyst material can be conveniently prepared in two steps. In a first step a lower oligomeric alkyl molybdate is prepared by contacting an inorganic molybdenum compound with an excess of an aliphatic monohydric alcohol in the presence of an effective amount of a weak base at a temperature sufficient to cause the molybdenum containing compound to become substantially dissolved in the alcohol. In a second step the lower oligomeric alkyl molybdate prepared in the first step is oxidized with an oxidizing amount of molecular oxygen at temperatures in the range of from about 60° C to about 200° C to form the oxidized alkyl molybdate complex catalyst material used in the method of the instant invention.

The inorganic molybdenum compounds that can be utilized in forming the lower oligomeric alkyl molybdate can be generally any molybdic oxide, acid, or anhydride. Additionally, as will be more fully detailed hereinafter, complex molybdate salts of ammonium compounds can be utilized. Examples of suitable inorganic molybdenum compounds include molybdenum trioxide, molybdenum heteropolyoxides, molybdic acid, molybdenum anhydride, ammonium molybdate, ammonium paramolybdate and mixtures thereof.

The alcohols that can be used in preparing the lower alkyl molybdates are generally primary or secondary monohydric alcohols containing from about 6–30 carbon atoms. The alcohols may be straight chain, branched chain or alicyclic in nature. Examples of suitable such monohydric compounds include hexyl alcohol, cyclohexyl alcohol, octyl alcohol, 2-ethylhexanol and the like. The higher aliphatic alcohols, i.e., those containing greater than 9 carbon atoms, are preferred primarily because they provide the final catalyst material with desirable solubility and stability characteristics in the epoxidation reaction mixture. Preferred alcohols include nonyl alcohol, isononyl alcohol, decyl alcohol, isodecyl alcohol and tridecyl alcohol and mixtures thereof. There are no required concentration ranges for the molybdates to the alcohol except that the alcohol must be in excess.

The preparation of the lower oligomeric molybdate is initially carried out in the presence of an effective amount of a weak base which preferably contains a basic nitrogen moiety. The basic substance is preferably ammonia or an amine wherein one or more of the labile hydrogens has been replaced with a hydrocarbon radical containing from about 1 to 25 carbon atoms. Examples of such compounds are monomethylamine, triethylamine, diethylamine, cyclohexylamine, and the like.

In accordance with a greatly preferred method of preparation, the above oligomeric alkyl molybdate is the reaction product of an ammonium salt of a complex molybdate such as ammonium molybdate or ammonium paramolybdate and a monohydric alcohol. When utilizing this method, the molybdenum containing compounds also contain a basic nitrogen moiety in the form of a cation of a complex molybdate salt. Thus, no additional basic material need be added. The most preferred salt is "85% molybdic acid" which is primarily ammonium paramolybdate.

The presence of the weak base is critical to the formation of the lower oligomeric alkyl molybdate of the instant invention. The exact reason for the criticality is not completely understood. However, it is known that the reaction product of the inorganic molybdenum containing compound and the molybdic alcohol in the presence of an effective amount of a weak base contains molybdenum in other than its higher oxidation states. The product is believed to contain lower oligomeric molybdate moieties such as dimers or trimers wherein the molybdenum molecules are bonded or complexed with sufficient oxygen to form a lower molybdenum valence state complex.

Determination of the effective amount of the weak base to be utilized in forming the lower oligomeric alkyl molybdate is somewhat empirical. However, it is generally sufficient to add up to a stoichiometric equivalent amount based upon the molybdenum compound. When an ammonium salt of a complex molybdate, or mixtures of inorganic molybdate compounds and the ammonium salt complex are used, additional basic material need not be added.

The temperature at which the lower oligomeric alkyl molybdate is prepared is generally that temperature which will result in the dissolution of the inorganic molybdenum containing compound within a reasonable period of time. Preferably the formation of the lower oligomeric alkyl molybdate is carried out at temperatures of from about 100° C to 250° C and at reaction times of from about 1–6 hours.

In the second step the lower oligomeric alkyl molybdate is oxidized with an oxidizing amount of oxygen. The oxidation may be carried out in any well known manner, at lower temperatures, wherein molecular oxygen is utilized as the oxidizing agent. The oxidation may be carried out as a separate step or can be performed in situ at the commencement of the epoxidation reaction. The molecular oxygen can be as an admixture with other nondeleterious gases, i.e., air or can be pure oxygen gas. Preferably oxidation is carried out in appropriate vessel by bubbling pure molecular oxygen through the crude reaction mixture obtained in step one. Since excess alcohol is utilized in forming the lower oligomeric alkyl molybdate, the alcohol acts as a solvent medium for the subsequent oxidation. The oxidation is effectively carried out at lower temperatures of from about 60° C to the boiling point of the solvent medium. The amount of oxygen and the time required to oxidize the catalyst of the instant invention is somewhat empirical but it can be generally easily estimated by the skilled artisan. Specifically, the oxidized solution will change color indicating a commencement of the change in oxidation state of the molybdenum contained in the complex. The solution when oxidized takes on a blue or a blue-black appearance when observed with the naked eye.

Generally, the direct oxidation of the crude lower oligomeric alkyl molybdate-alcohol reaction mixture at lower temperatures is somewhat time consuming. Expediently, the oxidation of the crude reaction mixture is accomplished at higher temperatures in the presence of an excess of a suitable nonpolar solvent. When this method of oxidation is utilized, the crude lower oligomeric alkyl molybdate-alcohol reaction mixture is initially dissolved in an excess of nonpolar solvent which is substantially stable under oxidation conditions. Suitable solvents include benzene, xylene, chlorobenzene, dichlorobenzene, $\alpha,\alpha,\alpha$-trifluorotoluene and the like. The reaction product solvent admixture is then subjected to an oxidizing amount of molecular oxygen, as hereinbefore described, at temperatures approaching the boiling point of the admixture.

Preferably, the solvent is selected to be compatible with the epoxidation reaction, such that the dissolved crude oxidized alkyl molybdate admixture formed upon oxidation can be directly utilized as the catalyst-solvent medium in performing the epoxidation. Thus, the solvent is preferably selected for compatibility in the epoxidation reaction as well as stability under epoxidation conditions. Solvent having a boiling point greater than 100° C are preferred. Chlorobenzene is the preferred solvent for oxidation when the solvent is to be further utilized as the epoxidation reaction medium solvent as will be more fully described hereinafter.

Further, it has been found expeditious to concentrate the lower oligomeric alkyl molybdate-alcohol crude reaction mixture prior to the oxidation step when a suitable nonpolar solvent is utilized. Specifically, the excess alcohol is removed by, for example, vacuum distillation to give a solution containing preferably more than about 20% by weight molybdenum. Although this concentration step is not necessary in preparing the catalyst of the instant invention, it is preferred. One advantage to initially concentrating the crude reaction mixture by removal of excess alcohol is the minimization of unwanted alcohol oxidation products which can more readily occur at the higher epoxidation temperatures realized when a solvent is utilized in the epoxidation step.

As previously mentioned, the lower oligomeric alkyl molybdates initially formed may be oxidized in situ directly in the epoxidation reaction without requiring a separate oxidation step; however, this is not preferred. Specifically, it has been found that oxidizing the lower oligomeric alkyl molybdate prior to charging the catalyst into the epoxidation system yields a much more stable catalyst thus minimizing sludge-forming decomposition products in the feed tanks and the reactor. Additionally, the catalyst oxidized in situ does not yield the performance reproducibility of the pre-oxidized material.

The olefinically unsaturated material that can be epoxidized in accordance with the instant invention are generally compounds having one aliphatic, olefinically-unsaturated carbon-carbon bond and containing from about 3 to about 30 carbon atoms. The olefinic reactant may be acyclic, monocyclic, bicyclic or polycyclic. Examples of suitable olefinic reactants include propylene, isobutylene, cyclohexene, hexene-2, octene-1, styrene and the like. This list should be considered as exemplary of those reactants which can be utilized within the scope of the invention and not exhaustive.

The preferred olefins in accordance with the invention are the lower olefins having from 3 to 4 carbon atoms in the aliphatic chain. This class of olefins are known in the art to be much more difficult to epoxidize than other olefins. It has been found that this class of olefins is epoxidized with particularly high conversion in an efficient manner in accordance with the method of the instant invention.

The epoxidation of the olefin reactant is accomplished by intimately contacting the olefin in liquid phase with an epoxidizing amount of a molecular oxygen epoxidizing agent. Gas, containing molecular oxygen, as an admixture with other nondeleterious gases, i.e., air may be used. It is preferred that pure oxygen gas be used. The amount of the molecular oxygen used in accordance with the instant method is somewhat empirical, but generally up to a stoichiometric amount of molecular oxygen can be used. For most applications and particularly when a continuous process is employed, an excess of the olefin material up to about 10 moles of olefin to about 1 mole of molecular oxygen is used. An amount in a range of from about 3 to about 5 moles of olefin to about 1 mole of molecular oxygen is preferred.

It is preferable to use a solubilizing amount of a suitable solvent to maintain the gaseous reactants and the catalyst in liquid phase thus providing a substantially homogeneous reaction system. Use of such solvents is well known in the art. In accordance with the inventive method, the amount of solvent utilized is generally that amount required to substantially dissolve the gaseous reactants, the catalyst, and the liquid olefin if one is utilized. Suitable solvents are generally nonpolar liquids which are substantially stable under epoxidation reactions and act as a solvent for reactants and the catalyst. Generally aromatic hydrocarbons or halogenated hydrocarbons are preferred. Examples are xylene, benzene, toluene, chlorobenzene, dichlorobenzene and the like. A greatly preferred solvent is chlorobenzene because of ease of recovery from lower oxirane reaction products and desirable boiling point.

The temperature at which the epoxidation reaction is carried out will depend somewhat upon the reactant catalyst employed but generally higher temperatures in the range of from about 210°-270° C and preferably temperatures of from about 230° C — 260° C are employed. The most preferred temperature is in the range of 250° C. Because of the high temperatures, the reaction pressures required to maintain the reactants, products and the like in substantially liquid phase are relatively higher than heretofore normally used in the art. Although the pressure need only be sufficient to maintain a substantially autogenous system, pressures in the range of from about 90 to about 110 atmospheres are convenient to effectively carry out the instant process. A pressure of about 100 atmospheres is preferred.

As was previously mentioned, the catalyst material shows unexpectedly high activity, while remaining stable, at the higher temperatures utilized in practicing the instant invention. These properties allow utilization of very short holding times in practicing the process while maintaining high conversion rates. Holding times in the range of from about 1 minute to about 2 minutes have been found particularly effective when the method is carried out in a continuous mode. The holding times for practicing the invention in semicontinuous or batch phase can be readily determined by the skilled artisan.

Catalytically effective amounts of catalyst for the epoxidation reaction range from about 5 to 1,000 parts per million (ppm) based on the total feedstock. Preferred ranges are between 10 and 100 ppm.

The epoxidation reaction is suitably conducted by any of a variety of procedures. The mode of conducting the epoxidation process is not critical and may be accomplished by conventional methods such as batch, continuous, or semicontinuous reactions. In accordance with one procedure, the olefin reactant and the catalyst are initially charged into a suitable vessel equipped for reflux. The vessel is heated to reaction temperature and molecular oxygen then metered into the reaction mixture with constant stirring. In another method the reaction is effected in a continuous manner such as by intimately contacting a catalyst/olefin solvent feed-stream with molecular oxygen in a suitable reaction chamber. In accordance with another method, the catalyst which has been dissolved in a suitable nonpolar solvent is charged into an autoclave which is then sealed and flushed with nitrogen. The olefinic compound and the molecular oxygen are then pressured into the sealed autoclave and the reaction mixture heated to reaction temperatures and stirred while reaction pressures are maintained.

At the conclusion of the reaction, the product mixture can be separated and the products recovered by conventional methods such as fractional distillations, selective extractions, filtration and the like. Further, the catalyst, unreacted reactants, and solvents can be recycled.

The invention will be further illustrated by the folowing specific examples which are given by way of illustration and not by way of limitation.

EXAMPLE I

This example shows the formation of the oxidized alkyl molybdate complex catalyst material utilized in the method of the instant invention. This example was carried out in essentially three steps wherein the lower oligomeric alkyl molybdate was initially formed in an excess of alcohol. The crude reaction product was then concentrated by removal of excess alcohol. Finally, the concentrated reaction product was dissolved in a suitable solvent and oxidized.

In the first step, a 1000 ml. clean, dry distilling flask equipped with a foam trap, magnetic stirring bar, and thermometer was charged with 20 g of powdered "85% molybdic acid" (primarily ammonium paramolybdate) and 220 g of isononyl alcohol. The mixture was heated under aspirator vacuum and the reflux temperature was adjusted to 140°-160° C by use of an air bleed regulated aspirator. After refluxing for one hour, most of the salt had dissolved to give a very dark yellow solution. after cooling to room temperature, the solution was filtered through an inorganic filter aid to remove residue and the filter pad was washed with an aliquot of isononyl alcohol. The filtrate recovered was 277 g of a dark brown homogeneous solution containing 3.97 wt. % molybdenum. (Calculated value: 3.93 wt. based upon the amount of inorganic molybdenum containing compound initially charged.)

In a second step, 100 g of the dark brown homogeneous solution prepared in step 1 was charged into a 500 ml. clean, dry, round bottom flask and placed on a small rotary evaporator under full pump vacuum. The sample was then heated at 70°-90° C on a water bath until essentially all excess alcohol was removed. The resulting 17 g of dark brown concentrate was recovered.

In a third step the 17 g of concentrate formed in step two was dissolved in 500 ml. of chlorobenzene and poured into a clean, dry 100 ml. 3-neck flask equipped with a magnetic stirring bar, oxygen sparger tube, condenser, and vent tube. The mixture was then refluxed at 130°-132° C while oxygen was continually metered into the flask contents (about 200–400 ml/min. for an hour). During the reflux period, the contents of the flask changed from brown to deep blue. At the end of oxidation a deep blue homogeneous solution was obtained which was subsequently cooled and concentrated on a steam bath under aspirator vacuum to yield a final product weighting 128 g. The solution contained 3.19 wt. % molybdenum (Calculated value: 3.1 wt. % based upon the amount of inorganic molybdenum containing compound initially charged.)

EXAMPLE II

In this example, a catalyst derived from ammonium molybdate and isononyl alchohol was again prepared in three steps substantially as in Example I. However, in this example aliquots of the product were analyzed after each step. After the first step, the dark brown homogeneous solution obtained was again concentrated as described in Example I until substantially all the excess alcohol was removed. A small sample was analyzed by atomic absorption spectroscopy and showed 22.2% by weight molybdenum as metal. The remaining unanalyzed concentrated residue was then oxidized in accordance with step 3 of Example I. A deep blue homogeneous solution was obtained. From the solution was isolated a solid dark blue crystalline material which contained 40.3% molybdenum by weight and had a molecular weight of 1,110 (vapor phase osmometry).

From this example, it can be seen that the lower oligomeric alkyl molybdate ester is essentially in a dimer or trimeric form and, as indicated by the color, is in a lower oxidized state. The oxidized alkyl molybdate ester complex, on the other hand, showed a dark blue color, which indicates a higher oxidation state of molybdenum which is believed to be predominantly the Mo(VI) state. The resulting oxidized molybdate complex has a content of molybdenum and molecular weight which indicates about 4–7 molybdenum moieties per complex. The above analysis was substantiated by infrared spectroscopy which showed the presence of Mo—O—R, Mo=O, Mo—O—Mo bonding arrangements.

EXAMPLE III

In this example the procedure of experiment II was identically repeated and the dark blue crystals isolated as in Example II. On analysis, the molybdenum content was shown to be 40.3 wt. %. This example shows the reproducibility of the catalyst preparation of the instant invention.

EXAMPLE IV

In this example, the preparation of Example I was essentially repeated, however, the solvent utilized in oxidation was dichlorobenzene instead of chlorobenzene. At the end of the oxidation step a blue-black concentrate having a molecular weight of 878 and a molybdenum content of 41.7 wt.. % was recovered. The solid showed slightly tacky or sticky characteristics, evidently indicating the presence of trapped solvent in the complex.

EXAMPLE V

This example shows the preparation of an oxidized catalyst material using tridecyl alcohol. To a clean, dry one-liter distilling flask equipped with a capillary air bleed and thermometer were added 10 g of ammonium molybdate and 150 g of tridecyl alcohol. The flask was attached to a 1 inches × 24 inches slivered, vacuum-jacketed column equipped with a reflux ratio controller. The mixture was refluxed under full pump vacuum (1-2 mm. Hg pressure with air bleed) for 1.5 hours.

About 40 to 50 ml of tridecyl alcohol was taken overhead at a 1:1 reflux ratio to form a condensed reaction production. The pot temperature was about 135°-140° C. The pot residues, which were not homogeneous, were filtered through a thin pad of inorganic filter aid. There was recovered 65 g of homogeneous, very dark yellow solution which appeared to be stable in air and was soluble in acetone and in cyclohexane.

To a clean, dry 1000 ml, 3-necked distilling flask equipped with a magnetic stirring bar, oxygen sparger tube, condenser, and vent tube were added 10 g of the molybdic acidtridecyl alcohol concentrate and 300 g chlorobenzene. The mixture was refluxed at 130°-132° C with continuous oxygen flow (about 200-400 ml/min.) for one hour. During the reflux period, the solution color changed from dark yellow to green and finally to dark blue. No solid residues formed either during or after the oxygen treatment. This oxygen treated material appeared to have better stability and solubility characteristics than the untreated concentrate.

EXAMPLES VI-VIII

The following table illustrates several other catalyst materials prepared substantially in accordance with the procedure of Example I which are within the scope of the instant invention. The molybdenum analysis reported in Table I is the molybdenum present in a concentrate after removal of excess alcohol. The concentrated catalyst or the catalyst in the original alcohol solution are both useful in the oxidation of olefins to olefin axides.

EXAMPLE IX

This experiment was preformed in a manner similar to that described in Example V, except 20 g of ammonium molybdate and 200 g of decyl alcohol were heated at a temperature of 115°-120° C for one hour, then at 130°-135° C for an additional hour. The reflux temperature was controlled by an air bleed-regulated aspirator vacuum.

Table I

| Ex. | Alcohol | Reaction temp. °C | Time min. | Mo converted to soluble form wt. % | Color of oxidized product | Mo in concentrate wt. % |
|---|---|---|---|---|---|---|
| VI | N-Decanol | 120-130 | 240 | 80-90 | Blue | 19.3 |
| VII | 2,6-Dimethyl-4-heptanol | 150, 135-140 | 120, 180 | 74 | Blue | 37.2 |
| VIII | 2,2-Dimethyl-1,pentanol | 150-155 | 120 | 44 | Blue | 26.3 |

After working up the product, there was obtained 219 g of dark yellow, homogeneous solution containing 3.6 wt. % molybdenum.

A 100 g sample of the homogeneous solution was then added to a 500 ml round bottom flask and placed on a small rotary evaporator under full pump vacuum. The sample was concentrated at 70°-90° C on a water bath until essentially all the excess alcohol was removed. Then 17 g of concentrate was dissolved in 500 ml of chlorobenzene, added to a 1000 ml 3-necked flask, and treated with oxygen as described in Example V. The deep-blue, homogeneous solution was then cooled and concentrated on a steam bath under aspirator vacuum to a final weight of 128 g. This solution contained 3.19 wt. % molybdenum. (Calculated value: 3.1 wt. %.)

EXAMPLE X

The following experiment was run to show the empirical nature of the molybdenum catalyst compound of the instant invention. To a 500 ml clean, dry distilling flask equipped with a thermometer, magnetic stirring bar, and foam trap was added 100 g tridecanol and 9 g ammonium paratungstate. The mixture was refluxed for an hour at 150° C under aspirator vacuum. At the end of this time little if any of the ammonium paratungstate had been dissolved. No identifiable tungstate product was observed.

EXAMPLE XI

In this example epoxidation of propylene was accomplished at higher temperatures and low holding times in accordance with the method of the instant invention. The catalyst was an oxidized ammonium molybdate-isononyl reaction product as prepared in Example I.

The apparatus used for this oxidation was a stirred, ceramic-lined, 500 ml. autoclave. Chlorobenzene containing catalyst material (28 ppn molybdenum) was premixed with oxygen and fed into the autoclave at two points: a connection, bottom center, where this feed was mixed with propylene, and a dip tube extending about half-way to the bottom of the autoclave. The autoclave was fitted with a cooling coil to provide close temperature control, and was equipped with a mechanical stirrer with three sets of propellers on the shaft. A product withdrawal tube at the top of the autoclave allowed the product to exit to a cooling coil and then through a back-pressure regulator to a gas-liquid separator where the off-gas was metered and sampled and the liquid product was retained for weighing and sampling. The solvent-filled reactor was heated to reaction temperature (250° C) with pressure being maintained at about 106 atmospheres and propylene was fed to the reactor for 10-15 min. before the oxygen was turned on. After the initial exotherm, about ¼ to 1 hour prerun, a steady state was achieved, the product was collected, and the off-gas was sampled. The feed rates for the reaction were as follows: chlorobenzene, 46.2 lbs/hr.; propylene, 8.32 lbs./hr.; oxygen, 564 g/hr. The average residence time was about 1.2 minutes. The yield of propylene oxide by chromatography, correcting for the heavy residues formed, was 57 mol % and the conversion based on propylene was 15 mol %. The residues/oxide wt. ratio was 0.11, the oxide/acids wt. ratio was 12.5 and the % residue was 0.22.

EXAMPLE XII

In this example various soluble metal catalysts, which are commercially available, were used in epoxidation of propylene using the method and apparatus described in Example XI. Additionally, the molybdenum isononyl complex as produced in accordance with Example I was run at 220° C as a comparison. The results are shown in Table II. Also as a comparison the results obtained in Example XI are shown in Table II.

As can be seen from the table, all of the prior art soluble catalyst material produced a substantial percentage of residue even at lower temperatures. Molybdenum naphthenate which proved to be the most active catalytic material shown a weight percent residue of 0.50. In contrast the molybdenum isononyl complex prepared in accordance with Example I at a slightly higher temperature but a much reduced holding time., i.e., less than half the holding time for the molybdenum naphthenate, showed a yield of 50.4 and a higher conversion. In addition, the weight percent residue obtained with the molybdenum isononyl complex was approximately half that obtained with the molybdenum naphthenate. Further, at the preferred temperature of 250° C, the catalyst complex of the instant invention, not only shows a higher calculated yield and higher conversion at a much reduced holding time, but also shows a substantially reduced weight residue. Thus, this example shows the unexpected activity and stability of the catalyst material used in accordance with the instant inventive process.

EXAMPLE XIII

In this example, a vanadium tridecanol catalyst compound was produced as follows. Initially a simple alkyl ortho vanadate was prepared by refluxing ammonium vanadate in an excess of tridecanol. A majority of excess alcohol was then removed by distillation to form a concentrate. The condensate was then oxidized as follows: 40 g of the tridecyl vanadate concentrate and 500 g of dichlorobenzene was added to a clean, dry 100 ml. 3-necked flask. The contents were brought to reflux and molecular oxygen bubbled through the refluxing material. Oxidation was continued in this manner for about one hour. No particular color change was noted during the oxidation but the solution appeared to be slightly ligher yellow after oxidation.

After cooling, the oxidized product was concentrated on a steam bath under aspirator vacuum to yield 79 g of a dark yellow liquid concentrate. Since no color change was noted, the procedure was repeated.

A second aliquot of 88 g of the simple ortho alkyl vanadate concentrate was added to 500 g of dichlorobenzene in a 1,000 ml. 3-necked flask. The flask contents were refluxed in the presence of a continual flow of pure oxygen for two hours. Again no appreciable change in color was noted. The oxidized product was then concentrated to about 150 ml. on a steam bath under respirator vacuum. The final concentrate weighed 250 g and was shown to contain 1-2% vanadium by weight.

The oxidized product prepared in the repeated oxidation was then used as a catalyst in an epoxidation reaction which was run substantially in accord with the procedure and using the apparatus of Example XI. Additionally, for comparison two other epoxidation reactions were run substantially in accord with the procedure and using the apparatus of Example XI, except for the catalyst material. The results are shown in Table III.

TABLE II

| Catalyst | Catalyst concentration | Solvent feed rate lbs./hr. | Propylene feed rate lbs./hr. | $O_2$ feed rate g/hr. | Temp. °C | Holding, time, min. | Propylene oxide conc. wt. % | GLC yield | Corr.* yield | Conv. | Wt. % residue | Wt. of residue, g |
|---|---|---|---|---|---|---|---|---|---|---|---|---|
| Chromium naphthenate[1] | 36 ppm | 45.20 | 8.52 | 564 | 210 | 2.6 | 1.14 | 46.2 | 33.1 | 10.6 | 0.98 | 52.0 |
| Copper octoate[1] | 36 ppm | 44.80 | 8.32 | 564 | 210 | 2.6 | 0.96 | 40.7 | 37.5 | 10.2 | 0.20 | 37.0 |
| Nickel octoate[1] | 37 ppm | 44.40 | 8.36 | 564 | 210 | 2.6 | 1.12 | 46.8 | 34.5 | 10.1 | 0.85 | 43.0 |
| Cobalt[2] linoresinate | 47 ppm | 44.60 | 8.16 | 564 | 210 | 2.6 | 1.23 | 48.0 | 42.5 | 11.1 | 0.33 | 26.0 |
| Cerrium naphthenate[1] | 30 ppm | 44.60 | 8.52 | 564 | 210 | 2.6 | 1.26 | 52.2 | 37.0 | 10.1 | 0.99 | 50.0 |
| Zerconium octoate[1] | 30 ppm | 44.80 | 8.48 | 564 | 210 | 2.6 | 1.31 | 52.4 | 39.1 | 10.6 | 0.85 | 53.0 |
| Vanadium naphthenate | 41 ppm | 44.00 | 8.64 | 564 | 210 | 2.6 | 0.88 | 38.3 | 32.7 | 9.3 | 0.40 | 28.0 |
| Molybdenum naphthenate | 38 ppm | 45.00 | 8.60 | 564 | 210 | 2.6 | 2.07 | 64.5 | 55.9 | 13.2 | 0.50 | 41.0 |
| Molybdenum isononyl complex[3] | 28 ppm | 47.20 | 8.28 | 564 | 220 | 1.2 | 1.83 | 54.2 | 50.4 | 15.0 | 0.26 | 21.0 |
| Molybdenum isononyl complex[3] | 28 ppm | 46.20 | 8.32 | 564 | 250 | 1.2 | 2.00 | 61.2 | 57.4 | 14.6 | 0.22 | 27.0 |

[1]The Shepherd Chemical Co., 500 Poplar Street, Cincinnati, Ohio 45212.
[2]The Harshaw Chemical Co., Division of Kewanee Oil Co., 1945 East 97th Street, Cleveland, Ohio 44106.
[3]Catalyst material of Example I.
*Corrected GLC yield taking into account residue formation.

TABLE III

| Catalyst | Catalyst concentration | Solvent feed rate lbs./hr. | Propylene feed rate lbs./hr. | O₂ feed rate g/hr. | Temp. °C | Holding time, min. | Propylene oxide conc. wt. % | GLC yield | Corr.* yield | Conv. | Wt. % residue | Wt. % residue g |
|---|---|---|---|---|---|---|---|---|---|---|---|---|
| A Oxidized vanadium tridecanol material | 37 ppm | 46.40 | 4.80 | 564 | 220 | 1.33 | 0.51 | 26.7 | 23.4 | 14.5 | 0.27 | 25.0 |
| | | 46.40 | 5.08 | 564 | 235 | 1.33 | 0.68 | 33.0 | 28.0 | 14.6 | 0.37 | 48.0 |
| | | 46.00 | 5.04 | 564 | 250 | 1.33 | 0.91 | 36.1 | 33.1 | 18.1 | 0.23 | 23.0 |
| B Oxidized molybdenum tridecanol complex | 20 ppm | 47.00 | 5.24 | 564 | 220 | 1.33 | 1.61 | 54.8 | 53.6 | 20.3 | 0.07 | 26.0 |
| | | 46.60 | 5.20 | 564 | 235 | 1.33 | 1.76 | 58.2 | 54.4 | 21.3 | 0.21 | 48.0 |
| | | 45.80 | 5.40 | 564 | 250 | 1.33 | 1.90 | 60.8 | 57.6 | 21.0 | 0.17 | 30.0 |
| C No catalyst | — | 47.00 | 4.76 | 564 | 220 | 1.33 | 1.28 | 47.3 | 42.5 | 20.7 | N/A | 27.0 |
| | | 46.60 | 4.96 | 564 | 235 | 1.33 | 1.46 | 52.4 | 45.1 | 20.3 | N/A | 48.0 |
| | | 46.80 | 4.96 | 564 | 250 | 1.33 | 1.54 | 54.8 | 48.2 | 20.5 | N/A | 29.0 |

*Corrected GLC yield taking into account residue formation.

As is shown in Table III, run B using the oxygen molybdenum tridecanol complex of the instant invention was far superior in every respect to run A using the oxidized vanadium tridecanol material even though a greater amount of the vanadium catalyst was used. In fact, the run using the oxidized vanadium tridecanol material catalyst was substantially inferior to run C using no catalyst.

EXAMPLE XIV

In this example, three epoxidation runs were made with a commercial molybdenum naphthenate catalyst in a 500 ml. ceramic coated reactor using a chlorobenzene solvent. The three runs were made at varying temperatures to show the instability of commercially prepared molybdenum naphthenate as a function of temperature as compared to the catalyst material of the instant invention. The results are shown in Table IV. It can be seen from Table IV the holding time had been appropriately reduced to make the residue numbers more meaningful and comparable with prior examples of the catalyst of the instant invention. It will be noted that reduction in holding time substantially reduces the GLC yield and the actual calculated yield of the prior art molybdenum naphthenate catalyst material.

EXAMPLE XV

In this example numerous epoxidation reactions were run using various catalyst materials of the instant invention. The reactions were run using the method and apparatus described in Example XI. The results are shown in Table V.

TABLE V

| Catalyst | Catalyst concentration | Solvent feed rate lbs./hr. | Propylene feed rate lbs./hr. | O₂ feed rate g/hr. | Temp. °C | Holding time, min. | Propylene oxide conc. wt. % | GLC yield | Corr.* yield | Conv. | Wt. % residue | Wt. % residue g |
|---|---|---|---|---|---|---|---|---|---|---|---|---|
| Molybdenum tridecanol complex | 57 ppm | 46.80 | 5.08 | 564 | 220 | 1.33 | 1.57 | 60.4 | 53.9 | 18.6 | 0.32 | 16.0 |
| | | 46.80 | 5.04 | 564 | 235 | 1.33 | 1.68 | 59.3 | 56.0 | 20.4 | 0.17 | 35.0 |
| | | 46.00 | 5.08 | 564 | 250 | 1.33 | 1.76 | 60.7 | 58.2 | 20.7 | 0.12 | 21.0 |
| Molybdenum n-decanol complex | 18 ppm | 46.80 | 5.04 | 564 | 220 | 1.33 | 1.67 | 52.7 | 46.3 | 22.7 | 0.44 | 18.5 |
| | | 46.80 | 4.96 | 564 | 240 | 1.33 | 1.85 | 56.8 | 55.3 | 24.0 | 0.10 | 34.0 |
| Molybdenum tridecanol complex | 20 ppm | 47.00 | 5.24 | 564 | 220 | 1.33 | 1.61 | 54.8 | 53.6 | 20.3 | 0.07 | 26.0 |
| | | 46.60 | 5.20 | 564 | 235 | 1.33 | 1.76 | 58.2 | 54.4 | 21.3 | 0.21 | 48.0 |
| | | 45.80 | 5.40 | 564 | 250 | 1.33 | 1.90 | 60.8 | 57.6 | 21.0 | 0.17 | 30.0 |
| Molybdenum isononyl alcohol complex | 28 ppm | 47.20 | 8.28 | 564 | 220 | 1.20 | 1.83 | 54.2 | 50.4 | 15.0 | 0.26 | 21.0 |
| | | 47.00 | 8.00 | 564 | 235 | 1.20 | 1.98 | 56.4 | 52.8 | 16.3 | 0.24 | 39.0 |
| | | 46.20 | 8.32 | 564 | 250 | 1.20 | 2.00 | 61.2 | 57.4 | 14.6 | 0.22 | 27.0 |

*Corrected GLC yield taking into account residue formation.

While the invention has been explained in relation to its preferred embodiment, it is to be understod that various modifications thereof will become apparent to those skilled in the art upon reading the specification and is intended to cover such modifications as fall within the scope of the appended claims.

What is claimed is:

1. A method for epoxidizing olefins to the corresponding oxirane in liquid phase, which comprises the step of:

intimately contacting an olefinically unsaturated compound with an epoxidizing amount of a molecular oxygen epoxidizing agent in the presence of a solubilizing amount of a suitable nonpolar solvent and a catalytically effective amount of an oxidized alkyl molybdate complex at epoxidizing temperatures of from about 210° C to about 270° C and at pressures sufficient to maintain the reaction mixture consisting essentially of the olefin, solvents, products and by-products substantially in liquid phase, wherein

TABLE IV

| Catalyst | Catalyst concentration | feed rate lbs./hr. | Propylene feed rate lbs./hr. | O₂ feed rate g/hr. | Temp. °C | Holding time, min. | Propylene oxide conc. wt. % | GLC yield | Corr.* yield | Conv. | Wt. % residue | Wt. % residue g |
|---|---|---|---|---|---|---|---|---|---|---|---|---|
| Molybdenum naphthenate | 30 ppm | 30.40 | 9.04 | 564 | 190 | 1.60 | 2.07 | 48.5 | 43.3 | 12.0 | 0.52 | 70.0 |
| | | 30.20 | 8.48 | 564 | 210 | 1.60 | 2.25 | 49.3 | 41.4 | 14.0 | 0.87 | 51.0 |
| | | 31.20 | 8.24 | 564 | 230 | 1.60 | 2.50 | 57.8 | 46.6 | 13.7 | 1.05 | 61.0 |

*Corrected GLC yield taking into account residue formation.

said oxidized alkyl molybdate complex is prepared by initially forming a lower oligomeric alkyl molybdate, by heating a compound selected from a group consisting of ammonium molybdate, ammonium paramolybdate, 85% molybdic acid and mixtures thereof with an excess of a primary or secondary aliphatic monohydric alcohol having from about 6 to about 30 carbon atoms to a temperature sufficient to substantially dissolve said molybdate; and oxidizing said lower oligomeric alkyl molybdate with an oxidizing amount of molecular oxygen.

2. The method of claim 1 wherein said oxidizing is accomplished in situ at the commencement of an epoxidation reaction.

3. The method of claim 1 wherein said oxidizing is accomplished by contacting the lower oligomeric alkyl molybdate compound with an oxidizing amount of molecular oxygen at temperatures of from about 60° C. to about 200° C.

4. The method of claim 1 wherein said aliphatic monohydric alcohol is selected from a group consisting of nonyl alcohol, isononyl alcohol, decyl alcohol, isodecyl alcohol, tridecyl alcohol and mixtures thereof.

5. The method of claim 4 wherein said contacting takes place in the presence of a solubilizing amount of a non-polar solvent selected from aromatic hydrocarbons and chlorinated aromatic hydrocarbons having a boiling point greater than 100° C.

* * * * *